United States Patent [19]

Fischer et al.

[11] Patent Number: 4,760,843
[45] Date of Patent: Aug. 2, 1988

[54] CONNECTOR FOR FRACTURED BONES

[76] Inventors: Artur Fischer, Weinhalde 34, D-7244 Waldachtal 3/Tumlingen; Wolfgang Kramer, Feldbergstrasse 10, D-7031 Oberjettingen, both of Fed. Rep. of Germany

[21] Appl. No.: 884,103

[22] Filed: Jul. 2, 1986

[30] Foreign Application Priority Data

Jul. 12, 1985 [DE] Fed. Rep. of Germany ... 8520206[U]
Oct. 28, 1985 [DE] Fed. Rep. of Germany ....... 3538238

[51] Int. Cl.$^4$ ............................................. A61F 5/04
[52] U.S. Cl. .................. 128/92 YF; 411/57; 411/128; 411/60
[58] Field of Search ............ 128/92 R, 92 YF, 92 YP; 411/57, 60, 71, 72, 128, 395

[56] References Cited

U.S. PATENT DOCUMENTS

| | | | |
|---|---|---|---|
| 1,021,390 | 3/1912 | Wagner | 411/57 |
| 1,136,638 | 4/1915 | Zifferer | 411/60 |
| 1,138,219 | 5/1915 | Hottenroth | 411/57 |
| 1,922,120 | 8/1933 | Brosig | 411/60 |
| 2,026,686 | 1/1936 | Kirley | 411/57 |
| 2,370,327 | 2/1945 | Rosan | 411/57 |
| 2,455,885 | 12/1948 | Theurer | 411/57 |
| 2,871,749 | 2/1959 | Kalb | 411/57 |
| 3,022,701 | 2/1962 | Potruch | 411/57 |
| 3,081,808 | 3/1963 | Rosan et al. | 411/178 |
| 3,230,994 | 1/1966 | Rosan | 411/178 |
| 3,279,519 | 10/1966 | Neuschotz | 411/178 |
| 3,281,173 | 10/1966 | Rosan | 411/178 |
| 3,383,975 | 5/1968 | Cushman | 411/57 |
| 3,413,887 | 12/1968 | Von Wolff et al. | 411/60 |
| 3,435,526 | 4/1969 | Brancato | 128/92 YF |
| 3,896,504 | 7/1975 | Fischer | 128/92 YF |
| 4,011,602 | 3/1977 | Rybicki et al. | 128/92 YF |
| 4,408,938 | 10/1983 | Maguire | 411/57 |
| 4,484,570 | 11/1984 | Suther et al. | 128/92 YP |
| 4,488,843 | 12/1984 | Achille | 411/60 |
| 4,611,581 | 9/1986 | Steffee | 128/69 |

Primary Examiner—C. Fred Rosenbaum
Assistant Examiner—Colleen M. Reilly
Attorney, Agent, or Firm—Michael J. Striker

[57] ABSTRACT

A connector for osteosynthesis, especially for fastening bone fragments comprises a plug sleeve and a screw engageable in the plug sleeve, the plug sleeve being formed of a viscoplastic, tissue-compatible plastics and having a thread shape on its outer surface. The plug sleeve can be slightly expanded at its end facing the head of the screw and also expanded to a greater extent at its other end, so that simple assembly and firm clamping in the bone tissue is achieved. It is possible to monitor the position of the plug sleeve in the bone constantly during assembly on an X-ray screen in conjunction with a metallic screwdriver or a measuring scale provided on the screwdriver for screwing the sleeve into the bone.

10 Claims, 2 Drawing Sheets

Fig. 5
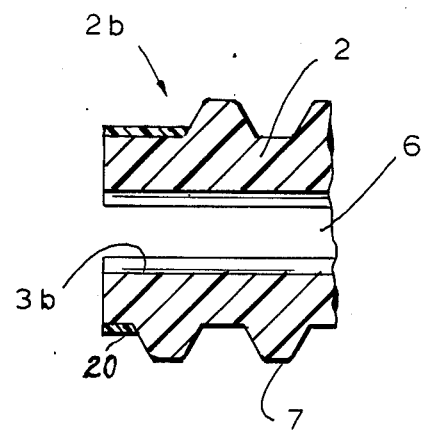
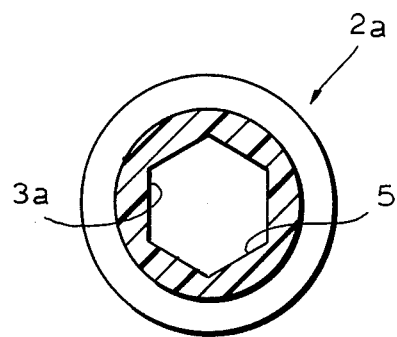
Fig. 4

CONNECTOR FOR FRACTURED BONES

BACKGROUND OF THE INVENTION

The present invention relates to a connector or fastening element for osteosynthesis, particularly for fastening bone fragments using a support plate.

Depending on the type of bone fracture, draw-in bolts are used directly or in combination with support plates for fixing bone fragments. Depending upon the location in which they are to be used, cortical or spongiosal screws which have different forms of thread are used. The spongiosal screws have a very pronounced, deep thread in order to achieve an adequate hold in the very soft bone tissue. The disadvantage of these screws, however, is that they are very difficult to unscrew, particularly from the cortical substance, once the fracture has mended. A further disadvantage in directly fastening bones together, using screws is that the direct connection between the screw and the bone is inflexible. Brief overstressing of the bone results in damage to the connection, which can lead to loosening the screws or possibly even breaking out.

Connectors of the foregoing type are known. One of such connectors is disclosed in applicant's U.S. Pat. No. 3,678,925.

SUMMARY OF THE INVENTION

It is an object of the present invention to provide an improved connector for osteosynthesis.

The invention is based on the idea of providing a fastening element or connector for osteosynthesis, which allows high pull-out values and is capable of resiliently absorbing overstressing, and is easy to assemble and dismantle.

These and other objects of the invention are attained by a connector for fractured bones, comprising a plug sleeve adapted for inserting into a fractured bone bridging the fracture thereof, and having a leading portion adapted to be located in one bone fragment and a trailing portion adapted to communicate with the other bone fragment; and an expander screw insertable and engageable in said plug sleeve, said plug sleeve having an outer surface having a shape of a thread, said sleeve being expandable at said leading portion and at said trailing portion, said screw having a head which is faced by said trailing portion in assembly.

For the placement of the connector in a fractured bone, a bore, corresponding in diameter approximately to the core diameter of the plug sleeve, is formed in the bone. Using a thread tap, a thread which approximately corresponds in pitch and profile to the thread of the plug sleeve is cut in the bone. Using a screwdriver or a hexagonal key which engages in a shaped portion of the plug sleeve, the plug sleeve can then be screwed in the region of the fracture to such an extent that the plug sleeve comes to rest in the region on the far side of the fracture. It can often be necessary for the bore for receiving the plug sleeve to completely penetrate the cortical substance of the remote fragment in order to obtain a secure fastening. When the screw is screwed into the plug sleeve, the plug sleeve is slightly opened out at the trailing end facing the head of the screw, so that the plug sleeve is clamped at least to such an extent that it cannot turn when the screw is screwed in. In this manner the plug sleeve is reliably prevented from turning when the screw is screwed in and, as a result, altering its position or even emerging from the bone again at the end of bore opposite the head of the screw. As the screw is screwed in, the thread crests of the screw in the trailing part of the internal bore cut slightly into the inner wall of the plug sleeve, which is made from a tissue-compatible plastics, and thus effect the above mentioned expansion. The leading portion of the plug sleeve is also opened out or expanded.

The expansion means may be provided at said trailing portion and said leading portion, respectively, the expansion means at said trailing portion being able to open out said trailing portion to a lesser degree than the expansion means at said leading portion.

The leading portion is expanded considerably more as the screw is screwed in further, the thread turns of the plug sleeve in this area being pressed firmly into the bone tissue, so that plug sleeve is fixed so that it is capable of bearing high loads. The head of the screw lies against the fragment close to the head or against an additional support plate mentioned above and effects the clamping of the adjacent fragments in the region of the fracture surface.

Since the opening out or expansion that takes place at the trailing end of the plug sleeve when the screw is screwed in, has the sole purpose of preventing a further rotation of the plug sleeve, only a slight opening out or expansion occurs here.

The plug sleeve may have an internal through bore which has a smaller diameter in said leading portion than that in said trailing portion.

A portion of said internal bore made in said trailing portion may be slightly smaller in diameter than the outer diameter of the thread of said screw and the diameter of a portion of said internal bore, made in said leading portion, is smaller than a core diameter of said screw.

The different degrees of expansion in the two end regions of the plug sleeve are achieved due to the fact that the internal diameter in the trailing portion is noticeably larger than the internal diameter in the leading portion.

The expansion means at said leading portion may be formed by at least one first longitudinal slot extending from a leading end of said sleeve over a part of its length and the expansion means at said trailing portion may be formed by at least one second longitudinal slot extending from a trailing end of said sleeve over a part of its length and being shorter than said first longitudinal slot.

The plug sleeve preferably has at each of its two ends two opposing longitudinal slots which allow expansion when the screw is introduced. In the trailing region the length of the slot can constitute, for example, between 1/10 and 1/5 of the length of the plug sleeve, whilst in the leading portion the longitudinal slots extend, for example, as far as the center of the plug sleeve.

After the bore has been made in the bone fragments and the thread for the plug sleeve has been made by means of a thread tap, the plug sleeve can be screwed into the bore with a screwdriver.

A stop may be provided at a transition between the portion of said internal bore in said leading portion and the portion of the internal bore in said trailing portion, said internal bore having a shaped portion for receiving therein a screwdriver of a corresponding shape, said shaped portion extending via a defined distance up to said stop against which a tip of the screwdriver rests when the plug sleeve is screwed in.

The plug sleeve may be of such a length that the tip of the screwdriver can be pushed into the sleeve exactly as far as a leading end thereof.

The screwdriver for screwing in the plug sleeve may have a shaft provided with a length measuring scale which indicates the distance at least to the tip of the screwdriver and to the leading end of the plug sleeve.

The shaped portion of the sleeve bore may be a hexagonal socket. While being inserted into the sleeve the screwdriver obtains a defined position in the plug sleeve, so that the length measuring scale provided on the screwdriver shaft indicates exactly the distance to the above mentioned stop or, if the scale is adapted accordingly, the distance to the leading end of the plug sleeve. The insertion depth of the plug sleeve can in this manner be read out on the length measuring scale when the plug sleeve is screwed in. Furthermore, it is also possible to follow the insertion of the plug sleeve by means of an X-ray apparatus, since the position of the tip of the screwdriver can be followed. As a result of the defined position of the tip of the screwdriver inside the plug sleeve, it is possible to conclude the correspondingly exact position of the plug sleeve.

The screwdriver shaft can, in the leading region, be matched to the entire internal shaped portion of the plug sleeve, so that the tip of the screwdriver lies exactly at the leading end of the plug sleeve when the plug sleeve is screwed in.

In order to follow the exact position of the plug sleeve on the screen of an X-ray apparatus, the plug sleeve can also be at least partially metallized. This can be obtained by applying a coating to a part of the outer surface of the plug sleeve. The plug sleeve, consisting, for example, of a polyethylene of ultrahigh molecular weight, cannot be detected in an X-ray image. The metal sheathing, formed of a stainless steel, is used in order to be able to monitor the fitting of the plug sleeve or to locate the plug sleeve, and it can be applied to the nonexpanding part of the plug sleeve either in the form of a sleeve or by vacuum evaporation.

The thread crests and the thread troughs of the plug sleeve thread may be rounded. Rounding the thread profile protects the bone tissue against damage as the plug sleeve is screwed in.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 4 is a sectional view on line IV—IV of FIG. 1; and FIG. 5 is a portion V of the connector of FIG. 1, on enlarged scale.

DETAILED DESCRIPTION OF THE PREFERRED EMBODIMENT

Figure 1:
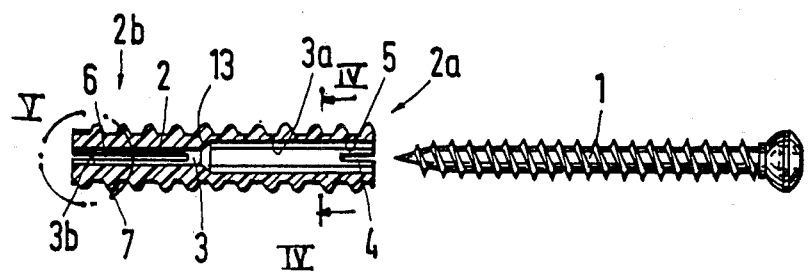
FIG. 1 shows an exploded view of the connector according to the invention.

Referring now to the drawings in detail the connector for fractured bones according to the invention comprises an expander or draw-in screw 1 of stainless steel and a plug sleeve 2 which is formed of a tissue-compatible plastic, for example polyethylene of ultrahigh molecular weight. Sleeve 2 has an internal bore 3 the rear portion of which has the diameter which is slightly smaller than the external diameter of the thread of expander screw 1. The thread crests therefore cut slightly into the inner wall of the plug sleeve 2 when screw 1 is screwed into the sleeve. At the same time, a slight opening out or expansion is provided in the region of the trailing portion 2a of the plug sleeve. The plug sleeve thus has in that region of the trailing portion 2a two opposing longitudinal slots 4 which allow opening out or expansion of the plug sleeve 2.

The internal bore 3 of the sleeve further has a portion 3a which is provided with a hexagonal socket 5 which serves the purpose of the placement of a hexagonal key or a screwdriver of corresponding shape. From the portion 3a, the internal bore 3 tapers to a diameter that is smaller than the core diameter of the screw 1. This smaller portion of bore 3 is designated at 3b. In the region of a leading portion 2b of the plug sleeve 2, the plug sleeve has two opposing longitudinal slots 6 which extend approximately over half the length of the plug sleeve 2, so that this region is expanded when the screw 1 is screwed in. Since the longitudinal slots 6 are significantly longer than the longitudinal slots 4 at the rear end of the plug sleeve and since the internal diameter of the sleeve in the region of the longitudinal slots 6 is substantially smaller than that in the region of the longitudinal slots 4 there is a significantly greater expansion at the forward portion 2b than that in the trailing portion 2a when the screw 1 is screwed into the plug sleeve 2. This opening out or expansion, in the region of the trailing portion 2a serves to secure the plug sleeve 2 against undesired twisting when the screw 1 is screwed in, whilst the opening out in the region of the leading portion 2b effects the actual clamping of the plug sleeve 2 in the bone, so that the plug sleeve 2 is still held securely in the bone even in the case of strong tightening of the screw 1 and the resulting high tensile forces.

The outer surface of the plug sleeve 2 is provided over its entire length with a thread 7, the thread crests and thread troughs of which are rounded. The plug sleeve 2 can have an unthreaded portion (not shown here) to which a metal coating is applied which enables the plug sleeve to be detected in an X-ray image.

To fix the connector or fastening element in the bone first of all, a bore corresponding approximately to the core diameter of the plug sleeve 2 is drilled. Using a thread tap, a thread, which corresponds to the thread 7 of the plug sleeve 2, is then made in the bone tissue. In order to keep destruction of the bone tissue to a minimum, the thread tap has a leading cutting portion and an adjoining, thread-shaping portion. Such a thread tap is described in German Patent Application No. P 35 24 946.3.

Figure 2:
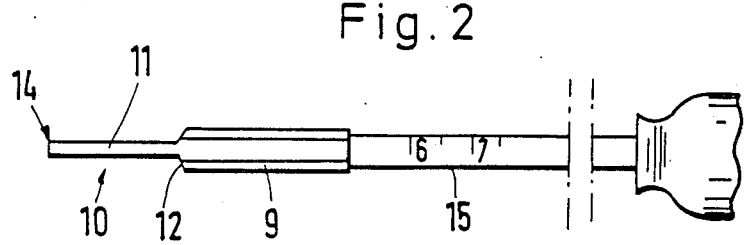
FIG. 2 illustrates a screwdriver for drawing in the plug sleeve of the connector shown in FIG. 1.
Figure 3:
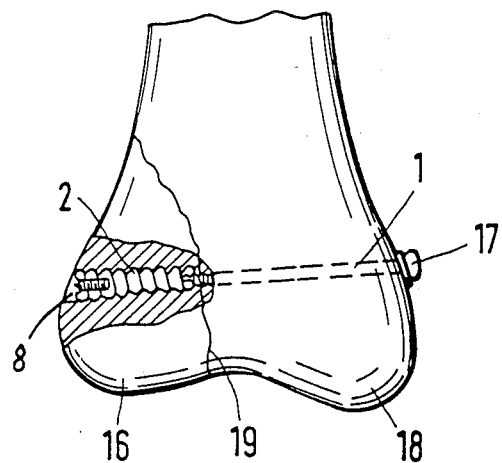
FIG. 3 is the connector in the assembled condition, anchored in the bone.

Using the screwdriver shown in FIG. 2, the plug sleeve 2 can be screwed into a threaded bore 8, as shown in FIG. 3. For this purpose the screwdriver has a hexagonal shaped portion 9 which corresponds to the hexagonal socket 5 formed in the plug sleeve 2. At the forward end 10 the screwdriver merges into a rod-shaped end piece 11 the diameter of which matches the internal diameter of leading portion 2b of the plug sleeve. The screwdriver can then be inserted into the plug sleeve 2 unless a transition portion 12, which borders the hexagonal shaped portion 9, rests against a corresponding stop 13 provided in the plug sleeve 2. The tip 14 of the screwdriver then lies in the same plane as the forward end of the plug sleeve 2. Since the screwdriver is made of metallic material, the position of the plug sleeve when the latter is screwed in, can all the time be followed on an X-ray screen. The tip 14 of the screwdriver at the same time indicates the position of the leading end of the plug sleeve 2. In addition, it is possible to provide on a shaft 15 of the screwdriver a measuring scale on which the particular insertion depth of the plug sleeve 2 can be read out.

The screwdriver can also be manufactured without the rod-shaped portion 11, then it would be possible for the measuring scale to be arranged on the shaft 15 in such a manner that the length measuring scale would indicate the distance to the forward end of the plug sleeve.

FIG. 3 shows the position of the plug sleeve 2 in a bone fragment 16 on the far side of the fracture, whilst the head 17 of the screw rests against a bone fragment 18 on the near side of the fracture. The plug sleeve 2 is located in a through bore and is anchored securely in the bone fragment 16, especially as a result of the expansion pressure in the leading portion 2b. By using such a plug sleeve it is possible to achieve a high bearing pressure in the region of the fracture surface 19.

When the fracture has mended, the screw 1 is unscrewed again, so that, again, using a suitable screwdriver or hexagonal key, the plug sleeve 2 can be unscrewed from the threaded bore formed in the bone. The plug sleeve 2 is partially covered with a metal coating 20, as shown in FIG. 5.

It will be understood that each of the elements described above, or two or more together, may also find a useful application in other types of connectors for fractured bones differing from the types described above.

While the invention has been illustrated and described as embodied in a connector for fractured bones, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A connector for fractured bones, comprising a plug sleeve adapted for inserting into a bore formed in a fractured bone for bridging the fracture thereof, and having a leading portion adapted to be located in one bone fragment and a trailing portion adapted to communicate with the other bone fragment; an expander screw insertable and engageable in said plug sleeve, said plug sleeve having an outer surface having a shape of a thread, said sleeve being expandable at said leading portion and at said trailing portion, said screw having a head which is faced by said trailing portion in assembly; and expansion means provided at said trailing portion and said leading portion, respectively, the expansion means at said trailing portion being able to open said trailing portion to a lesser degree that the expansion means at said leading portion.

2. The connector as defined in claim 1, wherein said plug sleeve has an internal through bore which has a smaller diameter in said leading portion than that in said trailing portion.

3. The connector as defined in claim 1, wherein a portion of said internal bore, made in said trailing portion is slightly smaller in diameter than an outer diameter of the thread of said screw, and the diameter of a portion of said internal bore made in said leading portion is smaller than a core diameter of said screw.

4. The connector as defined in claim 1, wherein the expansion means at said leading portion are formed by at least one first longitudinal slot extending from a leading end of said sleeve over a part of its length, and the expansion means at said trailing portion are formed by at least one second longitudinal slot extending from a trailing end of said sleeve over a part of its length and being shorter than said first longitudinal slot.

5. The connector as defined in claim 3, wherein a stop is provided at a transition between the portion of said internal bore in said leading portion and the portion of the internal bore in said trailing portion, said internal bore having a shaped portion for receiving therein a screwdriver of a corresponding shape, said shaped portion extending via a defined distance up to said stop against which a tip of the screwdriver rests when the plug sleeve is screwed in.

6. The connector as defined in claim 5, wherein said shaped portion is a hexagonal socket.

7. The connector as defined in claim 1, wherein said plug sleeve is formed of viscoplastic tissue-compatible plastics.

8. The connector as defined in claim 7, wherein said plug sleeve is at least partially covered with metal coating.

9. A connector for fractured bones, comprising a plug sleeve adapted for inserting into a bore formed in a fractured bone for bridging the fracture thereof, and having a leading portion adapted to be located in one bone fragment and a trailing portion adapted to communicate with the other bone fragment; an expander screw insertable and engageable in said plug sleeve, said plug sleeve having an outer surface having a shape of a thread, said sleeve being expandable at said leading portion and at said trailing portion, said screw having a head which is faced by said trailing portion in assembly; and expansion means provided at said trailing portion and said leading portion, respectively, the expansion means at said trailing portion being able to open said trailing portion to a lesser degree that the expansion means at said leading portion, the expansion means at said leading portion being formed by at least one first longitudinal slot extending from a leading end of said sleeve over a part of its length, and the expansion means at said trailing portion being formed by at least one second longitudinal slot extending from a trailing end of said sleeve over a part of its length and being shorter than said first longitudinal slot.

10. A connector for fractured bones, comprising a plug sleeve adapted for inserting into a bore formed in a fractured bone for bridging the fracture thereof, and having a leading portion adapted to be located in one bone fragment and a trailing portion adapted to communicate with the other bone fragment; an expander screw insertable and engageable in said plug sleeve, said plug sleeve having an outer surface having a shape of a thread, said sleeve being expandable at said leading portion and at said trailing portion, said screw having a head which is faced by said trialing portion in assembly; and expansion means provided at said trailing portion and said leading portion, respectively, the expansion means at said trailing portion being able to open said trailing portion to a lesser degree that the expansion means at said leading portion, the expansion means at said leading portion being formed by two opposing first longitudinal slots extending from a leading end of said sleeve over a part of its length, and the expansion means at said trailing portion being formed by two opposing second longitudinal slots extending from a trailing end of said sleeve over a part of its length and being shorter than said first longitudinal slots.

* * * * *